United States Patent
Peng et al.

(10) Patent No.: US 10,487,031 B2
(45) Date of Patent: Nov. 26, 2019

(54) AZEOTROPIC COMPOSITIONS COMPRISING HYDROGEN FLUORIDE AND FLUOROCARBONS

(71) Applicant: The Chemours Company FC, LLC, Wilmington, DE (US)

(72) Inventors: Sheng Peng, Hockessin, DE (US); Jeffrey Knapp, Wilmington, DE (US)

(73) Assignee: THE CHEMOURS COMPANY FC, LLC, Wilmington, DE (US)

(*) Notice: Subject to any disclaimer, the term of this patent is extended or adjusted under 35 U.S.C. 154(b) by 0 days.

(21) Appl. No.: 16/126,442

(22) Filed: Sep. 10, 2018

(65) Prior Publication Data

US 2019/0077734 A1    Mar. 14, 2019

Related U.S. Application Data

(60) Provisional application No. 62/556,783, filed on Sep. 11, 2017.

(51) Int. Cl.
| | | |
|---|---|---|
| C07C 19/10 | (2006.01) | |
| C07C 19/08 | (2006.01) | |
| C07C 21/18 | (2006.01) | |
| C01B 7/19 | (2006.01) | |
| C07C 19/12 | (2006.01) | |
| C09K 5/04 | (2006.01) | |
| H01B 3/56 | (2006.01) | |

(52) U.S. Cl.
CPC .............. C07C 21/18 (2013.01); C01B 7/191 (2013.01); C07C 19/10 (2013.01); C07C 19/12 (2013.01); C09K 5/044 (2013.01); C09K 5/045 (2013.01); H01B 3/56 (2013.01); C09K 2205/126 (2013.01); C09K 2205/32 (2013.01)

(58) Field of Classification Search
None
See application file for complete search history.

(56) References Cited

U.S. PATENT DOCUMENTS

| | | | | |
|---|---|---|---|---|
| 6,521,803 B1* | 2/2003 | Lambert | ................. | C01B 7/195 570/177 |
| 8,148,584 B2 | 4/2012 | Hedrick et al. | | |
| 8,486,293 B2* | 7/2013 | Knapp | .................... | C01B 7/196 252/67 |
| 9,328,042 B2 | 5/2016 | Peng et al. | | |

(Continued)

FOREIGN PATENT DOCUMENTS

| | | |
|---|---|---|
| CN | 103193586 | 7/2013 |
| CN | 104370690 | 2/2015 |

(Continued)

OTHER PUBLICATIONS

International Search Report and Written Opinion in International Application No. PCT/US2018/050232, dated Nov. 23, 2018, 12 pages.

(Continued)

*Primary Examiner* — Medhanit W Bahta

(57) ABSTRACT

The present application discloses compositions comprising hydrogen fluoride and fluorinated compounds (e.g., hydrofluorocarbons), wherein the fluorinated compound is present in the composition in an amount effective to form an azeotrope composition or azeotrope-like composition with the hydrogen fluoride.

23 Claims, 3 Drawing Sheets

(56) References Cited

U.S. PATENT DOCUMENTS

| | | | |
|---|---|---|---|
| 2001/0021792 A1 | 9/2001 | Nakada et al. | |
| 2007/0100175 A1* | 5/2007 | Miller | C01B 7/196 |
| | | | 570/178 |
| 2011/0101264 A1 | 5/2011 | Knapp | |
| 2012/0215039 A1 | 8/2012 | Hulse et al. | |
| 2012/0305382 A1* | 12/2012 | Knapp | C07C 21/18 |
| | | | 203/67 |
| 2019/0040321 A1* | 2/2019 | Knapp | C09K 3/14 |

FOREIGN PATENT DOCUMENTS

| | | |
|---|---|---|
| CN | 104072333 B | 4/2016 |
| WO | WO 2011/119370 | 9/2011 |
| WO | WO 2015/142981 | 9/2015 |
| WO | WO 2017/027323 | 2/2017 |

OTHER PUBLICATIONS

Zhang et al., "Synthesis of Z-1,1,1,4,4,4-hexafluoro-2-butene from Hexachlorobutadiene," Journal of Fluorine Chemistry, 2016, 191: 77-93.

* cited by examiner

AZEOTROPIC COMPOSITIONS COMPRISING HYDROGEN FLUORIDE AND FLUOROCARBONS

CROSS-REFERENCE TO RELATED APPLICATIONS

This application claims the benefit of U.S. Provisional Application Ser. No. 62/556,783, filed Sep. 11, 2017, the disclosure of which is incorporated herein by reference in its entirety.

TECHNICAL FIELD

This invention relates to compositions comprising hydrogen fluoride and hydrofluoroolefin (HFO), hydrofluorocarbon (HFC) or hydrochlorofluorocarbon (HCFC) compounds, wherein the hydrofluoroolefin, hydrofluorocarbon or hydrochlorofluorocarbon is present in the composition in an amount effective to form an azeotrope composition or azeotrope-like composition with the hydrogen fluoride.

BACKGROUND

Many industries have been working for the past few decades to find replacements for the ozone depleting chlorofluorocarbons (CFCs) and hydrochlorofluorocarbons (HCFCs). The CFCs and HCFCs have been employed in a wide range of applications, including their use as aerosol propellants, refrigerants, cleaning agents, expansion agents for thermoplastic and thermoset foams, heat transfer media, gaseous dielectrics, fire extinguishing and suppression agents, power cycle working fluids, polymerization media, particulate removal fluids, carrier fluids, buffing abrasive agents, and displacement drying agents. In the search for replacements for these versatile compounds, many industries have turned to the use of hydrofluorocarbons (HFCs) and hydrofluoroolefins (HFOs).

SUMMARY

The present application provides, inter alia, a composition comprising:
i) hydrogen fluoride; and
ii) a compound of Formula I:

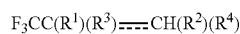

$F_3CC(R^1)(R^3)\!=\!=\!CH(R^2)(R^4)$    I wherein constituent members are defined herein and wherein the compound of Formula I is present in an amount effective to form an azeotrope composition or an azeotrope-like composition with the hydrogen fluoride.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting.

All publications, patent applications, patents, sequences, database entries, and other references mentioned herein are incorporated by reference in their entirety. In case of conflict, the present specification, including definitions, will control.

DETAILED DESCRIPTION

Figure 1:
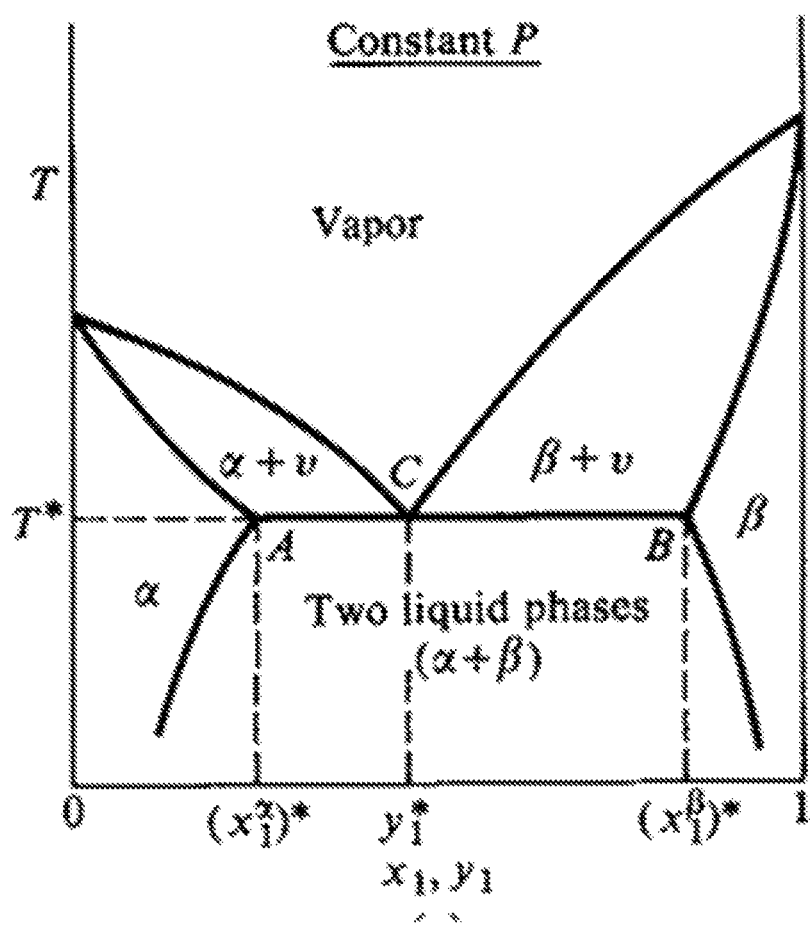
FIG. 1 shows an exemplary vapor-liquid equilibrium plot representative of the properties of heterogeneous azeotropes.

The HFCs do not contribute to the destruction of stratospheric ozone, but are of concern due to their contribution to the "greenhouse effect", i.e., they contribute to global warming. As a result of their contribution to global warming, the HFCs have come under scrutiny, and their widespread use may also be limited in the future. Thus, there is a need for compositions that do not contribute to the destruction of stratospheric ozone and also have low global warming potentials (GWPs). Certain hydrofluoroolefins, such as 1,1,1,4,4,4-hexafluoro-2-butene ($CF_3CH\!=\!CHCF_3$, HFO-1336mzz), meets both goals. For example, (Z)-HFO-1336mzz (i.e., (Z)-1,1,1,4,4,4-hexafluoro-2-butene) and (E)-HFO-1336mzz (i.e., (E)-1,1,1,4,4,4-hexafluoro-2-butene) are useful in many applications (e.g., a foam expansion agent or refrigerant) due to its low GWP, non-flammability, high efficiency, and thermal stability.

The formation of azeotropic or azeotrope-like compositions comprising hydrogen fluoride and the compounds described herein (e.g., compounds of Formula I) allow said compounds to be removed more easily and at lower temperatures from other higher boiling by-products formed, for example, in the synthesis of (E)-1,1,1,4,4,4-hexafluoro-2-butene and/or (Z)-1,1,1,4,4,4-hexafluoro-2-butene, allowing for improved purification of the desired products at lower energy and reduced cost. Additionally, said azeotropic compositions can be used in azeotropic distillations to remove hydrogen fluoride from higher boiling compounds that also form azeotropes with hydrogen fluoride. Exemplary processes for preparing (E)-1,1,1,4,4,4-hexafluoro-2-butene and/or (Z)-1,1,1,4,4,4-hexafluoro-2-butene may be found, for example, in U.S. patent application Ser. No. 15/124,738; and the U.S. patent application associated with The Chemours Company FC LLC, Reference No.: FL 1789, filed Sep. 11, 2017, the disclosures of each of which are incorporated herein by reference in their entireties.

Definitions and Abbreviations

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

As used herein, the term "about" is meant to account for variations due to experimental error (e.g., plus or minus approximately 10% of the indicated value). All measurements reported herein are understood to be modified by the term "about", whether or not the term is explicitly used, unless explicitly stated otherwise.

When an amount, concentration, or other value or parameter is given as either a range, preferred range or a list of upper preferable values and/or lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range.

Global warming potential (GWP) is an index for estimating relative global warming contribution due to atmospheric emission of a kilogram of a particular greenhouse gas compared to emission of a kilogram of carbon dioxide. GWP can be calculated for different time horizons showing the effect of atmospheric lifetime for a given gas. The GWP for the 100-year time horizon is commonly the value referenced.

As recognized in the art, an azeotropic composition is an admixture of two or more different components which, when in liquid form and (1a) under a given constant pressure, will boil at a substantially constant temperature, which temperature may be higher or lower than the boiling temperatures of the individual components, or (1b) at a given constant temperature, will boil at a substantially constant pressure, which pressure may be higher or lower than the boiling pressure of the individual components, and (2) will boil at substantially constant composition, which phase compositions, while constant, are not necessarily equal. (See, e.g., M. F. Doherty and M. F. Malone, Conceptual Design of Distillation Systems, McGraw-Hill (New York), 2001, 185).

A homogeneous azeotrope, in which a single vapor phase is in equilibrium with a single liquid phase, has, in addition to properties (1a), (1b), and (2) above, the property that the composition of each component is the same in each of the coexisting equilibrium phases. The general term "azeotrope" is a commonly used alternative name for a homogeneous azeotrope.

A heterogeneous azeotrope, in which a single vapor phase is in equilibrium with two liquid phases, has properties (1a), (1b), and (2) as described above where, while constant, the three coexisting equilibrium phases each have different compositions (See e.g., M. F. Doherty and M. F. Malone, Conceptual Design of Distillation Systems, McGraw-Hill (New York), 2001, 352). At the heterogeneous azeotrope, the composition of the overall liquid phase, (i.e., the liquid phase composition obtained by combining the two equilibrium liquid phases), is identical to the composition of the equilibrium vapor phase.

The properties of heterogeneous azeotropes are described, for example, in FIG. 1. As shown in FIG. 1, temperature T* is the minimum temperature at which both vapor and liquid phases occur. Below T*, depending on composition, liquid phase α, liquid phase β, or both α and β will exist. When the liquid composition lies within the (α+β) region, it splits into two separate liquid phases whose compositions are defined by the intersection of the solid lines starting at points A and B and continuing toward the bottom of FIG. 1 and a horizontal line at the specified temperature (FIG. 1). Above T*, in regions (α+ν) and (β+ν), a single liquid phase is in equilibrium with a vapor phase whose compositions are indicated by the intersection of the solid lines bounding region (α+ν) or (β+ν), depending on the mixture composition, and a horizontal line at the specified temperature. At temperature T*, three phases of different compositions, denoted by A, B, and C in FIG. 1, are in equilibrium with each other. Any mixture with a liquid phase composition between $(x_1^\alpha)^*$ and $(x_1^\beta)^*$ as shown in FIG. 1 will (I) separate into two liquid phases with compositions equal to $(x_1^\alpha)^*$ and $(x_1^\beta)^*$, (II) be in equilibrium with a vapor phase of composition $y_1^*$, and (III) boil at the same temperature T*. Points A, B, and C and temperature T* of FIG. 1 constitute the three equilibrium phases of a heterogeneous azeotrope. At the azeotropic composition, the overall liquid phase composition equals $y_1^*$.

As used herein, an "azeotrope-like" composition refers to a composition that behaves like an azeotropic composition (i.e., has constant boiling characteristics or a tendency not to fractionate upon boiling or evaporation). Hence, during boiling or evaporation, the vapor and liquid compositions, if they change at all, change only to a minimal or negligible extent. In contrast, the vapor and liquid compositions of non-azeotrope-like compositions change to a substantial degree during boiling or evaporation.

As used herein, the terms "azeotrope-like" or "azeotrope-like behavior" refer to compositions that exhibit dew point pressure and bubble point pressure with virtually no pressure differential. In some embodiments, the difference in the dew point pressure and bubble point pressure at a given temperature is 3% or less. In some embodiments, the difference in the bubble point and dew point pressures is 5% or less.

The term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified.

Throughout the definitions, the term "$C_{n-m}$" indicates a range which includes the endpoints, wherein n and m are integers and indicate the number of carbons. Examples include $C_{1-4}$, $C_{1-6}$, and the like.

As used herein, the term "$C_{n-m}$ alkyl" refers to a saturated hydrocarbon group that may be straight-chain or branched, having n to m carbons. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl, and the like. In some embodiments, the alkyl group has 1 to 6, 1 to 4, 1 to 3, or 1 to 2 carbon atoms.

As used herein, "halo" refers to fluoro, chloro, bromo, or iodo. In some embodiments, the halo is chloro or fluoro. In some embodiments, the halo is chloro.

As used herein, the term "$C_{n-m}$ haloalkyl" refers to an alkyl group having from one halogen atom to 2s+1 halogen atoms which may be the same or different, where "s" is the number of carbon atoms in the alkyl group, wherein the alkyl group has n to m carbon atoms. In some embodiments, the haloalkyl group is fluorinated only (i.e., a partially fluorinated alkyl or a perfluorinated alkyl). In some embodiments, the haloalkyl group has 1 to 6, 1 to 4, 1 to 3, or 1 to 2 carbon atoms.

Chemicals, Abbreviations, and Acronyms
HCFC-346mdf or 346mdf: 2-chloro-1,1,1,4,4,4-hexafluorobutane
347mef: 1,1,1,2,4,4,4-heptafluorobutane
356mff: 1,1,1,4,4,4-hexafluorobutane
HFIB or 1336 ft: 3,3,3-trifluoro-2-(trifluoromethyl)prop-1-ene
HFO-(E)-1336mzz or E-1336mzz: (E)-1,1,1,4,4,4-hexafluoro-2-butene
HFO-(Z)-1336mzz or Z-1336mzz: (Z)-1,1,1,4,4,4-hexafluoro-2-butene
CFC: chlorofluorocarbon
HCFC: hydrochlorofluorocarbon
HFC: hydrofluorocarbon
HFO: hydrofluoroolefin
NRTL: Non-Random, Two-Liquid
VLE: vapor-liquid equilibrium
Compositions The present application provides a composition, comprising:
i) hydrogen fluoride; and
ii) a compound of Formula I:

$$F_3CC(R^1)(R^3)\text{=}CH(R^2)(R^4) \quad \text{I}$$

wherein ==== refers to a single bond or a double bond;
$R^1$ is H, halo, or $C_{1-3}$ haloalkyl;
$R^2$ is H or $C_{1-3}$ haloalkyl; and
$R^3$ and $R^4$ are each H; or alternatively, $R^3$ and $R^4$ are absent when ==== forms a double bond;
wherein the compound of Formula I is present in an amount effective to form an azeotrope composition or an azeotrope-like composition with the hydrogen fluoride.

In some embodiments, $R^1$ is H, halo, or $C_{1-3}$ haloalkyl.
In some embodiments, $R^1$ is H, halo, or $C_{1-3}$ fluoroalkyl.
In some embodiments, $R^1$ is H, chloro, fluoro, or $C_{1-3}$ fluoroalkyl.
In some embodiments, $R^1$ is H, chloro, fluoro, or trifluoromethyl.
In some embodiments, $R^2$ is H or $C_{1-3}$ haloalkyl.
In some embodiments, $R^2$ is H or $C_{1-3}$ fluoroalkyl.
In some embodiments, $R^2$ is H or trifluoromethyl.
In some embodiments, the compound of Formula I is a compound of Formula Ia:

$$\underset{R^1}{\overset{F_3C}{\diagdown}}\!\!\!\!\!\!\!\!\!\diagup\!\!\!\!\!\!\!\!\!\overset{R^2}{\diagup} \quad \text{Ia}$$

In some embodiments, the compound of Formula I is a compound of Formula Ib or Formula Ic:

$$\underset{R^1}{\overset{F_3C}{\diagdown}}\!\!\!\!=\!\!\!\!\overset{R^2}{\diagup} \quad \text{Ib}$$

$$\underset{R^1}{\overset{F_3C}{\diagdown}}\!\!\!\!=\!\!\!\!\overset{}{\diagdown}\overset{R^2}{} \quad \text{Ic}$$

In some embodiments, the compound of Formula I is selected from the group consisting of:
1,1,1,4,4,4-hexafluorobut-2-ene;
3,3,3-trifluoro-2-(trifluoromethyl)prop-1-ene; 2-chloro-1,1,1,4,4,4-hexafluorobutane; 1,1,1,2,4,4,4-heptafluorobutane; and 1,1,1,4,4,4-hexafluorobutane;
wherein the compound of Formula I is present in an amount effective to form an azeotrope or an azeotrope-like composition with the hydrogen fluoride.

In some embodiments, the compound of Formula I is selected from the group consisting of:
(E)-1,1,1,4,4,4-hexafluorobut-2-ene;
(Z)-1,1,1,4,4,4-hexafluorobut-2-ene;
3,3,3-trifluoro-2-(trifluoromethyl)prop-1-ene;
2-chloro-1,1,1,4,4,4-hexafluorobutane;
1,1,1,2,4,4,4-heptafluorobutane; and
1,1,1,4,4,4-hexafluorobutane;
wherein the compound of Formula I is present in an amount effective to form an azeotrope or an azeotrope-like composition with the hydrogen fluoride.

In some embodiments, the compound of Formula I is (E)-1,1,1,4,4,4-hexafluorobut-2-ene, wherein the (E)-1,1,1,4,4,4-hexafluorobut-2-ene is present in an amount effective to form an azeotrope or an azeotrope-like composition with the hydrogen fluoride. In some embodiments, the (E)-1,1,1,4,4,4-hexafluorobut-2-ene is present in an amount effective to form an azeotrope with the hydrogen fluoride.

In some embodiments, the composition comprises from about 52 to about 76 mole percent hydrogen fluoride, for example, about 52 to about 70, about 52 to about 65, about 52 to about 60, about 52 to about 55, about 55 to about 76, about 55 to about 70, about 55 to about 65, about 55 to about 60, about 60 to about 76, about 60 to about 70, about 60 to about 65, about 65 to about 76, about 65 to about 70, or about 70 to about 76 mole percent hydrogen fluoride, and from about 48 to about 24 mole percent (E)-1,1,1,4,4,4-hexafluorobut-2-ene, for example, about 48 to about 30, about 48 to about 35, about 48 to about 40, about 48 to about 45, about 45 to about 24, about 45 to about 30, about 45 to about 35, about 45 to about 40, about 40 to about 24, about 40 to about 30, about 40 to about 35, about 35 to about 24, about 35 to about 30, or about 30 to about 24 mole percent (E)-1,1,1,4,4,4-hexafluorobut-2-ene.

In some embodiments, the composition comprising hydrogen fluoride and (E)-1,1,1,4,4,4-hexafluorobut-2-ene has a boiling point of from about −30° C. to about 110° C., for example, about −30° C. to about 100° C., about −30° C. to about 75° C., about −30° C. to about 50° C., about −30° C. to about 25° C., about −30° C. to about 0° C., about 0° C. to about 110° C., about 0° C. to about 100° C., about 0° C. to about 75° C., about 0° C. to about 50° C., about 0° C. to about 25° C., about 25° C. to about 110° C., about 25° C. to about 100° C., about 25° C. to about 75° C., about 25° C. to about 50° C., about 50° C. to about 110° C., about 50° C. to about 100° C., about 50° C. to about 75° C., about 75° C. to about 110° C., about 75° C. to about 100° C., or about 100° C. to about 110° C., at a pressure of from about 3 psia to about 812 psia, for example, about 3 psia to about 700 psia, about 3 psia to about 500 psia, about 3 psia to about 300 psia, about 3 psia to about 100 psia, about 100 psia to about 812 psia, about 100 psia to about 700 psia, about 100 psia to about 500 psia, about 100 psia to about 300 psia, about 300 psia to about 812 psia, about 300 psia to about 700 psia, about 300 psia to about 500 psia, about 500 psia to about 812 psia, about 500 psia to about 700 psia, or about 700 psia to about 812 psia.

In some embodiments, the compound of Formula I is (Z)-1,1,1,4,4,4-hexafluorobut-2-ene, wherein the (Z)-1,1,1, 4,4,4-hexafluorobut-2-ene is present in an amount effective to form an azeotrope or an azeotrope-like composition with the hydrogen fluoride.

In some embodiments, the composition comprises from about 59 to about 92 mole percent hydrogen fluoride, for example, about 59 to about 85, about 59 to about 75, about 59 to about 65, about 65 to about 92, about 65 to about 85, about 65 to about 75, about 75 to about 92, about 75 to about 85, or about 85 to about 92 mole percent hydrogen fluoride and from about 41 to about 8 mole percent (Z)-1,1,1,4,4,4-hexafluorobut-2-ene, for example, about 41 to about 15, about 41 to about 25, about 41 to about 35, about 35 to about 8, about 35 to about 15, about 35 to about 25, about 25 to about 8, about 25 to about 15, or about 15 to about 8 mole percent (Z)-1,1,1,4,4,4-hexafluorobut-2-ene.

In some embodiments, the composition comprising hydrogen fluoride and (Z)-1,1,1,4,4,4-hexafluorobut-2-ene has a boiling point of from about −30° C. to about 130° C., for example, about −30° C. to about 100° C., about −30° C. to about 75° C., about −30° C. to about 50° C., about −30° C. to about 25° C., about −30° C. to about 0° C., about 0° C. to about 130° C., about 0° C. to about 100° C., about 0° C. to about 75° C., about 0° C. to about 50° C., about 0° C. to about 25° C., about 25° C. to about 130° C., about 25° C. to about 100° C., about 25° C. to about 75° C., about 25° C. to about 50° C., about 50° C. to about 130° C., about 50° C. to about 100° C., about 50° C. to about 75° C., about 75° C. to about 130° C., about 75° C. to about 100° C., or about 100° C. to about 130° C., at a pressure of from about 2 psia to about 836 psia, for example, about 2 psia to about 800 psia, about 2 psia to about 600 psia, about 2 psia to about 400 psia, about 2 psia to about 200 psia, about 2 psia to about 100 psia, about 100 psia to about 836 psia, about 100 psia to about 800 psia, about 100 psia to about 600 psia, about 100 psia to about 400 psia, about 100 psia to about 200 psia, about 200 psia to about 836 psia, about 200 psia to about 800 psia, about 200 psia to about 600 psia, about 200 psia to about 400 psia, about 400 psia to about 836 psia, about 400 psia to about 800 psia, about 400 psia to about 600 psia, about 600 psia to about 836 psia, about 600 psia to about 800 psia, or about 800 psia to about 836 psia.

In some embodiments, the compound of Formula I is 3,3,3-trifluoro-2-(trifluoromethyl)prop-1-ene, wherein the 3,3,3-trifluoro-2-(trifluoromethyl)prop-1-ene is present in an amount effective to form an azeotrope or an azeotrope-like composition with the hydrogen fluoride.

In some embodiments, the composition comprises from about 45 to about 72 mole percent hydrogen fluoride, for example, about 45 to about 65, about 45 to about 55, about 55 to about 72, about 55 to about 65, or about 65 to about 72 mole percent hydrogen fluoride and from about 55 to about 28 mole percent 3,3,3-trifluoro-2-(trifluoromethyl) prop-1-ene, for example, about 55 to about 35, about 55 to about 45, about 45 to about 28, about 45 to about 35, or about 35 to about 28 mole percent 3,3,3-trifluoro-2-(trifluoromethyl)prop-1-ene.

In some embodiments, the composition comprising hydrogen fluoride and 3,3,3-trifluoro-2-(trifluoromethyl) prop-1-ene has a boiling point of from about −30° C. to about 140° C., for example, about −30° C. to about 100° C., about −30° C. to about 75° C., about −30° C. to about 50° C., about −30° C. to about 25° C., about −30° C. to about 0° C., about 0° C. to about 140° C., about 0° C. to about 100° C., about 0° C. to about 75° C., about 0° C. to about 50° C., about 0° C. to about 25° C., about 25° C. to about 140° C., about 25° C. to about 100° C., about 25° C. to about 75° C., about 25° C. to about 50° C., about 50° C. to about 140° C., about 50° C. to about 100° C., about 50° C. to about 75° C., about 75° C. to about 140° C., about 75° C. to about 100° C., or about 100° C. to about 140° C., at a pressure of from about 3 psia to about 800 psia, for example, about 3 psia to about 700 psia, about 3 psia to about 500 psia, about 3 psia to about 300 psia, about 3 psia to about 100 psia, about 100 psia to about 800 psia, about 100 psia to about 700 psia, about 100 psia to about 500 psia, about 100 psia to about 300 psia, about 300 psia to about 800 psia, about 300 psia to about 700 psia, about 300 psia to about 500 psia, about 500 psia to about 800 psia, about 500 psia to about 700 psia, or about 700 psia to about 800 psia.

In some embodiments, the compound of Formula I is 2-chloro-1,1,1,4,4,4-hexafluorobutane, wherein the 2-chloro-1,1,1,4,4,4-hexafluorobutane is present in an amount effective to form an azeotrope or an azeotrope-like composition with the hydrogen fluoride.

In some embodiments, the composition comprises from about 77 to about 97 mole percent hydrogen fluoride, for example, about 77 to about 95, about 77 to about 90, about 77 to about 85, about 85 to about 97, about 85 to about 95, about 85 to about 90, about 90 to about 97, about 90 to about 95, or about 95 to about 97 mole percent hydrogen fluoride, and from about 23 to about 3 mole percent 2-chloro-1,1,1, 4,4,4-hexafluorobutane, for example, about 23 to about 5, about 23 to about 10, about 23 to about 15, about 15 to about 3, about 15 to about 5, about 15 to about 10, about 10 to about 3, about 10 to about 5, or about 5 to about 3 mole percent 2-chloro-1,1,1,4,4,4-hexafluorobutane.

In some embodiments, the composition comprising hydrogen fluoride and 2-chloro-1,1,1,4,4,4-hexafluorobutane has a boiling point of from about −30° C. to about 140° C., for example, about −30° C. to about 100° C., about −30° C. to about 75° C., about −30° C. to about 50° C., about −30° C. to about 25° C., about −30° C. to about 0° C., about 0° C. to about 140° C., about 0° C. to about 100° C., about 0° C. to about 75° C., about 0° C. to about 50° C., about 0° C. to about 25° C., about 25° C. to about 140° C., about 25° C. to about 100° C., about 25° C. to about 75° C., about 25° C. to about 50° C., about 50° C. to about 140° C., about 50° C. to about 100° C., about 50° C. to about 75° C., about 75° C. to about 140° C., about 75° C. to about 100° C., or about 100° C. to about 140° C., at a pressure of from about 1 psia to about 510 psia, for example, about 1 psia to about 400 psia, about 1 psia to about 300 psia, about 1 psia to about 200 psia, about 1 psia to about 100 psia, about 1 psia to about 50 psia, about 50 psia to about 510 psia, about 50 psia to about 400 psia, about 50 psia to about 300 psia, about 50 psia to about 200 psia, about 50 psia to about 100 psia, about 100 psia to about 510 psia, about 100 psia to about 400 psia, about 100 psia to about 300 psia, about 100 psia to about 200 psia, about 200 psia to about 510 psia, about 200 psia to about 400 psia, about 200 psia to about 300 psia, about 300 psia to about 510 psia, about 300 psia to about 400 psia, or about 400 psia to about 510 psia.

In some embodiments, the compound of Formula I is 1,1,1,2,4,4,4-heptafluorobutane, wherein the 1,1,1,2,4,4,4- heptafluorobutane is present in an amount effective to form an azeotrope or an azeotrope-like composition with the hydrogen fluoride.

In some embodiments, the composition comprises from about 68 to about 89 mole percent hydrogen fluoride, for example about 68 to about 85, about 68 to about 80, about 68 to about 75, about 75 to about 89, about 75 to about 85, about 75 to about 80, about 80 to about 89, about 80 to about 85, or about 85 to about 89 mole percent hydrogen fluoride and from about 32 to about 11 mole percent 1,1,1,2,4,4,4-heptafluorobutane, for example, about 32 to about 15, about 32 to about 20, about 32 to about 25, about 25 to about 11, about 25 to about 15, about 25 to about 20, about 20 to about 11, about 20 to about 15, or about 15 to about 11 mole percent 1,1,1,2,4,4,4-heptafluorobutane.

In some embodiments, the composition comprising hydrogen fluoride and 1,1,1,2,4,4,4-heptafluorobutane has a boiling point of from about −30° C. to about 140° C., for example, about −30° C. to about 100° C., about −30° C. to about 75° C., about −30° C. to about 50° C., about −30° C. to about 25° C., about −30° C. to about 0° C., about 0° C. to about 140° C., about 0° C. to about 100° C., about 0° C. to about 75° C., about 0° C. to about 50° C., about 0° C. to about 25° C., about 25° C. to about 140° C., about 25° C. to about 100° C., about 25° C. to about 75° C., about 25° C. to about 50° C., about 50° C. to about 140° C., about 50° C. to about 100° C., about 50° C. to about 75° C., about 75° C. to about 140° C., about 75° C. to about 100° C., or about 100° C. to about 140° C., at a pressure of from about 1 psia to about 665 psia, for example, about 1 psia to about 600 psia, about 1 psia to about 400 psia, about 1 psia to about 200 psia, about 1 psia to about 100 psia, about 1 psia to about 50 psia, about 50 psia to about 665 psia, about 50 psia to about 600 psia, about 50 psia to about 400 psia, about 50 psia to about 200 psia, about 50 psia to about 100 psia, about 100 psia to about 665 psia, about 100 psia to about 600 psia, about 100 psia to about 400 psia, about 100 psia to about 200 psia, about 200 psia to about 665 psia, about 200 psia to about 600 psia, about 200 psia to about 400 psia, about 400 psia to about 665 psia, about 400 psia to about 600 psia, or about 600 psia to about 665 psia.

In some embodiments, the compound of Formula I is 1,1,1,4,4,4-hexafluorobutane, wherein the 1,1,1,4,4,4-hexafluorobutane is present in an amount effective to form an azeotrope or an azeotrope-like composition with the hydrogen fluoride.

In some embodiments, the composition comprises from about 57 to about 84 mole percent hydrogen fluoride, for example, about 57 to about 80, about 57 to about 75, about 57 to about 70, about 57 to about 65, about 65 to about 84, about 65 to about 80, about 65 to about 75, about 65 to about 70, about 70 to about 84, about 70 to about 80, about 70 to about 75, about 75 to about 84, about 75 to about 80, or about 80 to about 84 mole percent hydrogen fluoride and from about 43 to about 16 mole percent 1,1,1,4,4,4-hexafluorobutane, for example, about 43 to about 20, about 43 to about 25, about 43 to about 30, about 43 to about 35, about 35 to about 16, about 35 to about 20, about 35 to about 25, about 35 to about 30, about 30 to about 16, about 30 to about 20, about 30 to about 25, about 25 to about 16, about 25 to about 20, or about 25 to about 16 mole percent 1,1,1,4,4,4-hexafluorobutane.

In some embodiments, the composition comprising hydrogen fluoride and 1,1,1,4,4,4-hexafluorobutane has a boiling point of from about −30° C. to about 140° C., for example, about −30° C. to about 100° C., about −30° C. to about 75° C., about −30° C. to about 50° C., about −30° C. to about 25° C., about −30° C. to about 0° C., about 0° C. to about 140° C., about 0° C. to about 100° C., about 0° C. to about 75° C., about 0° C. to about 50° C., about 0° C. to about 25° C., about 25° C. to about 140° C., about 25° C. to about 100° C., about 25° C. to about 75° C., about 25° C. to about 50° C., about 50° C. to about 140° C., about 50° C. to about 100° C., about 50° C. to about 75° C., about 75° C. to about 140° C., about 75° C. to about 100° C., or about 100° C. to about 140° C., at a pressure of from about 1 psia to about 600 psia, for example, about 1 psia to about 400 psia, about 1 psia to about 200 psia, about 1 psia to about 100 psia, about 1 psia to about 50 psia, about 50 psia to about 600 psia, about 50 psia to about 400 psia, about 50 psia to about 200 psia, about 50 psia to about 100 psia, about 100 psia to about 600 psia, about 100 psia to about 400 psia, about 100 psia to about 200 psia, about 200 psia to about 600 psia, about 200 psia to about 400 psia, or about 400 psia to about 600 psia.

In some embodiments, the composition comprises:

from about 52 to about 76 mole percent hydrogen fluoride and from about 48 to about 24 mole percent (E)-1,1,1,4,4,4-hexafluorobut-2-ene, wherein the composition has a boiling point of from about −30° C. to about 110° C. at a pressure of from about 3 psia to about 812 psia; or from about 59 to about 92 mole percent hydrogen fluoride and from about 41 to about 8 mole percent (Z)-1,1,1,4,4,4-hexafluorobut-2-ene, wherein the composition has a boiling point of from about −30° C. to about 130° C. at a pressure of from about 2 psia to about 836 psia; or from about 45 to about 72 mole percent hydrogen fluoride and from about 55 to about 28 mole percent 3,3,3-trifluoro-2-(trifluoromethyl)prop-1-ene, wherein the composition has a boiling point of from about −30° C. to about 140° C. at a pressure of from about 3 psia to about 800 psia; or from about 77 to about 97 mole percent hydrogen fluoride and from about 23 to about 3 mole percent 2-chloro-1,1,1,4,4,4-hexafluorobutane, wherein the composition has a boiling point of from about −30° C. to about 140° C. at a pressure of from about 1 psia to about 510 psia; or from about 68 to about 89 mole percent hydrogen fluoride and from about 32 to about 11 mole percent 1,1,1,2,4,4,4-heptafluorobutane, wherein the composition has a boiling point of from about −30° C. to about 140° C. at a pressure of from about 1 psia to about 665 psia; or from about 57 to about 84 mole percent hydrogen fluoride and from about 43 to about 16 mole percent 1,1,1,4,4,4-hexafluorobutane, wherein the composition has a boiling point of from about −30° C. to about 140° C. at a pressure of from about 1 psia to about 600 psia.

In some embodiments, the composition provided herein is a homogeneous azeotrope.

In some embodiments, the composition provide herein is a heterogeneous azeotrope.

In some embodiments, the composition provided herein is an azeotrope-like composition.

EXAMPLES

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results.

Example 1. Vapor-Liquid Equilibrium Analysis

The PTx method is a known method for experimentally measuring vapor-liquid phase equilibrium (VLE) data of a mixture. The measurements can be made either isothermally or isobarically. The isothermal method requires measurement of the total pressure of mixtures of known composition at constant temperature. In this method, the total absolute pressure in a cell of known volume is measured at a constant temperature for various known compositions of the two compounds. The isobaric method requires measurement of the temperature of mixtures of known composition at constant pressure.

In this method, the temperature in a cell of known volume is measured at a constant pressure for various known compositions of the two compounds. Use of the PTx Method is described in detail in "Phase Equilibrium in Process Design", Wiley-Interscience Publisher, 1970, written by Harold R. Null, on pages 124 to 126, the disclosure of which is incorporated herein by reference in its entirety.

The measured data points can be converted into equilibrium vapor and liquid compositions in the PTx cell by using an activity coefficient equation model, such as the Non-Random, Two-Liquid (NRTL) equation, to represent liquid phase nonidealities. Use of an activity coefficient equation, such as the NRTL equation is described in detail in "The Properties of Gases and Liquids," 4th edition, published by McGraw Hill, written by Reid, Prausnitz and Poling, on pages 241 to 387, and in "Phase Equilibria in Chemical Engineering," published by Butterworth Publishers, 1985, written by Stanley M. Walas, pages 165 to 244, the disclosure of which is incorporated herein by reference in its entirety. Without wishing to be bound by any theory or explanation, it is believed that the NRTL equation, together with the PTx cell data, sufficiently predicts the vapor-liquid phase equilibrium behavior of the various mixture compositions of the present invention and as well as the behavior of these mixtures in multi-stage separation equipment such as distillation columns.

Example 2. Azeotropic Compositions of Hydrogen Fluoride and E-1336Mzz

Experimental PTx phase equilibrium data for HF and E-HFO-1336mzz was measured at 29.78° C., 76.71° C., and 79.34° C. The data was fit using the NRTL (non-random two-liquid) activity coefficient model and the resulting parameters used for modeling the mixture phase equilibrium. At a constant 29.78° C., the concentrations of E-1336mzz & HF in the mixture were varied in small increments and the corresponding equilibrium pressure was calculated at each liquid composition. Table 1 shows representative calculated points starting from pure E-1336mzz and slowly adding HF. Table 2 shows selected calculated points starting from pure HF and slowly adding E-1336mzz.

TABLE 1

| HF (mol %) | E-1336mzz (mol %) | Pressure (psia) |
|---|---|---|
| 0.00 | 100.00 | 33.35 |
| 1.00 | 99.00 | 35.63 |
| 5.00 | 95.00 | 41.47 |
| 10.00 | 90.00 | 46.14 |
| 20.00 | 80.00 | 50.05 |
| 30.00 | 70.00 | 50.64 |
| 40.00 | 60.00 | 50.82 |
| 50.00 | 50.00 | 50.95 |
| 51.00 | 49.00 | 50.85 |
| 55.00 | 45.00 | 50.85 |
| 60.00 | 40.00 | 50.85 |
| 70.00 | 30.00 | 50.85 |

TABLE 2

| HF (mol %) | E-1336mzz (mol %) | Pressure (psia) |
|---|---|---|
| 100.00 | 0.00 | 21.14 |
| 99.00 | 1.00 | 28.46 |
| 95.00 | 5.00 | 44.25 |
| 90.00 | 10.00 | 50.07 |
| 89.00 | 11.00 | 50.49 |
| 88.00 | 12.00 | 50.79 |
| 87.00 | 13.00 | 50.85 |
| 86.00 | 14.00 | 50.85 |
| 85.00 | 15.00 | 50.85 |
| 80.00 | 20.00 | 50.85 |
| 75.00 | 25.00 | 50.85 |
| 70.00 | 30.00 | 50.85 |

Tables 1 and 2 clearly show that, starting from both pure HF and pure E-1336mzz, the equilibrium pressure increased until it reached a maximum pressure of 50.85 psia and that, once reached, the 50.85 psia pressure continued to exist over a wide composition range. The existence of a pressure maximum in the mixture vapor-liquid phase equilibrium at constant temperature indicated that a maximum-pressure or, equivalently, a minimum-boiling azeotrope exists. The existence of the maximum equilibrium pressure (at constant temperature) over a wide composition range indicated that the azeotrope is heterogeneous. As confirmation, the presence of two liquid phases was visually observed during the phase equilibrium experiments. Based on Tables 1 & 2, at 29.78° C., azeotropic and/or azeotrope-like behavior exists from approximately 51.0 to 87.0 mole percent HF (49.0 to 13.0 mole percent E-1336mzz), where the equilibrium pressure is about 50.85 psia.

Since, in both homogeneous and heterogeneous azeotropes, the compositions of the equilibrium vapor and liquid phases (overall liquid phase composition for heterogeneous azeotropes) are equal, azeotropic compositions can be determined over a range of temperatures or pressures by: (1) measuring vapor-liquid equilibrium data over the full composition range at preferably two or more temperatures or pressures, (2) fitting the adjustable parameters of a vapor-liquid equilibrium model such as the Peng-Robinson equation of state and/or the NRTL equation to the experimental data, and (3) using the resulting model parameters to calculate vapor-liquid phase equilibrium and determine the point at which the vapor and liquid phase compositions are equal. This method was used to generate the following Table 3-4 and the azeotropic compositions described throughout the Examples. For mixtures that form heterogeneous azeotropes, unless stated otherwise, the reported liquid-phase compositions are those of the overall liquid phase.

TABLE 3

| Azeotropic Temperature (° C.) | Azeotropic Pressure (psia) | Vapor-Phase Composition (Mole Percent) | | Liquid-Phase Composition (Mole Percent) | |
|---|---|---|---|---|---|
| | | HF | E-1336mzz | HF | E-1336mzz |
| −30 | 3.84 | 75.33 | 24.67 | 75.33 | 24.67 |
| −20 | 6.54 | 72.76 | 27.24 | 72.76 | 27.24 |
| −10 | 10.64 | 70.31 | 29.69 | 70.31 | 29.69 |
| 0 | 16.60 | 68.06 | 31.94 | 68.06 | 31.94 |
| 10 | 25.03 | 64.73 | 35.27 | 64.73 | 35.27 |
| 20 | 36.24 | 63.40 | 36.60 | 63.40 | 36.60 |
| 30 | 51.23 | 61.90 | 38.10 | 61.90 | 38.10 |
| 40 | 70.68 | 60.51 | 39.49 | 60.51 | 39.49 |
| 50 | 95.55 | 59.20 | 40.80 | 59.20 | 40.80 |
| 60 | 126.94 | 57.96 | 42.04 | 57.96 | 42.04 |
| 70 | 166.26 | 56.63 | 43.37 | 56.63 | 43.37 |

TABLE 3-continued

| Azeotropic Temperature (° C.) | Azeotropic Pressure (psia) | Vapor-Phase Composition (Mole Percent) | | Liquid-Phase Composition (Mole Percent) | |
|---|---|---|---|---|---|
| | | HF | E-1336mzz | HF | E-1336mzz |
| 80 | 215.95 | 54.89 | 45.11 | 54.89 | 45.11 |
| 90 | 281.72 | 52.47 | 47.53 | 52.47 | 47.53 |
| 100 | 625.62 | 52.46 | 47.54 | 52.46 | 47.54 |
| 110 | 812.10 | 52.25 | 47.75 | 52.25 | 47.75 |

TABLE 4

| Azeotropic Temperature (° C.) | Azeotropic Pressure (psia) | Vapor-Phase Composition (Mass Percent) | | Liquid-Phase Composition (Mass Percent) | |
|---|---|---|---|---|---|
| | | HF | E-1336mzz | HF | E-1336mzz |
| −30 | 3.84 | 27.14 | 72.86 | 27.14 | 72.86 |
| −20 | 6.54 | 24.58 | 75.42 | 24.58 | 75.42 |
| −10 | 10.64 | 22.41 | 77.59 | 22.41 | 77.59 |
| 0 | 16.60 | 20.63 | 79.37 | 20.63 | 79.37 |
| 10 | 25.03 | 18.29 | 81.71 | 18.29 | 81.71 |
| 20 | 36.24 | 17.44 | 82.56 | 17.44 | 82.56 |
| 30 | 51.23 | 16.54 | 83.46 | 16.54 | 83.46 |
| 40 | 70.68 | 15.75 | 84.25 | 15.75 | 84.25 |
| 50 | 95.55 | 15.03 | 84.97 | 15.03 | 84.97 |
| 60 | 126.94 | 14.39 | 85.61 | 14.39 | 85.61 |
| 70 | 166.26 | 13.74 | 86.26 | 13.74 | 86.26 |
| 80 | 215.95 | 12.92 | 87.08 | 12.92 | 87.08 |
| 90 | 281.72 | 11.86 | 88.14 | 11.86 | 88.14 |
| 100 | 625.62 | 11.86 | 88.14 | 11.86 | 88.14 |
| 110 | 812.10 | 11.77 | 88.23 | 11.77 | 88.23 |

The calculated azeotropic ranges for HF/Z-1336mzz mixtures from −30° C. to 130° C. are summarized in Tables 5-6.

TABLE 5

| Azeotropic Temperature (° C.) | Azeotropic Pressure (psia) | Vapor-Phase Composition (Mole Percent) | | Liquid-Phase Composition (Mole Percent) | |
|---|---|---|---|---|---|
| | | HF | Z-1336mzz | HF | Z-1336mzz |
| −30 | 2.2 | 91.71 | 8.29 | 91.71 | 8.29 |
| −20 | 3.7 | 90.19 | 9.81 | 90.19 | 9.81 |
| −10 | 6.1 | 88.57 | 11.43 | 88.57 | 11.43 |
| 0 | 9.5 | 86.85 | 13.15 | 86.85 | 13.15 |
| 10 | 14.4 | 85.05 | 14.95 | 85.05 | 14.95 |
| 20 | 21.3 | 83.20 | 16.80 | 83.20 | 16.80 |
| 30 | 30.5 | 81.29 | 18.71 | 81.29 | 18.71 |
| 40 | 42.8 | 79.35 | 20.65 | 79.35 | 20.65 |
| 50 | 58.8 | 77.39 | 22.61 | 77.39 | 22.61 |
| 60 | 79.3 | 75.51 | 24.49 | 75.51 | 24.49 |
| 70 | 105.3 | 73.64 | 26.36 | 73.64 | 26.36 |
| 80 | 138.2 | 71.75 | 28.25 | 71.75 | 28.25 |
| 90 | 179.6 | 69.77 | 30.23 | 69.77 | 30.23 |
| 100 | 232.5 | 67.48 | 32.52 | 67.48 | 32.52 |
| 110 | 465.1 | 59.40 | 40.60 | 59.40 | 40.60 |
| 120 | 652.1 | 60.05 | 39.95 | 60.05 | 39.95 |
| 130 | 836.0 | 60.79 | 39.21 | 60.79 | 39.21 |

TABLE 6

| Azeotropic Temperature (° C.) | Azeotropic Pressure (psia) | Vapor-Phase Composition (Mass Percent) | | Liquid-Phase Composition (Mass Percent) | |
|---|---|---|---|---|---|
| | | HF | Z-1336mzz | HF | Z-1336mzz |
| −30 | 2.2 | 57.44 | 42.56 | 57.44 | 42.56 |
| −20 | 3.7 | 52.87 | 47.13 | 52.87 | 47.13 |
| −10 | 6.1 | 48.58 | 51.42 | 48.58 | 51.42 |
| 0 | 9.5 | 44.61 | 55.39 | 44.61 | 55.39 |
| 10 | 14.4 | 40.97 | 59.03 | 40.97 | 59.03 |
| 20 | 21.3 | 37.65 | 62.35 | 37.65 | 62.35 |
| 30 | 30.5 | 34.64 | 65.36 | 34.64 | 65.36 |
| 40 | 42.8 | 31.91 | 68.09 | 31.91 | 68.09 |
| 50 | 58.8 | 29.45 | 70.55 | 29.45 | 70.55 |
| 60 | 79.3 | 27.33 | 72.67 | 27.33 | 72.67 |
| 70 | 105.3 | 25.41 | 74.59 | 25.41 | 74.59 |
| 80 | 138.2 | 23.65 | 76.35 | 23.65 | 76.35 |
| 90 | 179.6 | 21.97 | 78.03 | 21.97 | 78.03 |
| 100 | 232.5 | 20.20 | 79.80 | 20.20 | 79.80 |
| 110 | 465.1 | 15.14 | 84.86 | 15.14 | 84.86 |
| 120 | 652.1 | 15.49 | 84.51 | 15.49 | 84.51 |
| 130 | 836.0 | 15.90 | 84.10 | 15.90 | 84.10 |

Example 4. Azeotropic Compositions of Hydrogen Fluoride and HFIB

The calculated azeotropic ranges for HF/HFIB (i.e., 1336 ft or 3,3,3-trifluoro-2-(trifluoromethyl)prop-1-ene) mixtures from −30° C. to 140° C. are summarized in Tables 7-8.

TABLE 7

| Azeotropic Temperature (° C.) | Azeotropic Pressure (psia) | Vapor-Phase Composition (Mole Percent) | | Liquid-Phase Composition (Mole Percent) | |
|---|---|---|---|---|---|
| | | HF | HFIB | HF | HFIB |
| −30 | 3.55 | 71.33 | 28.67 | 71.33 | 28.67 |
| −20 | 5.76 | 70.78 | 29.22 | 70.78 | 29.22 |
| −10 | 9.01 | 70.09 | 29.91 | 70.09 | 29.91 |
| 0 | 13.66 | 69.27 | 30.73 | 69.27 | 30.73 |
| 10 | 20.12 | 68.35 | 31.65 | 68.35 | 31.65 |
| 20 | 28.90 | 67.34 | 32.66 | 67.34 | 32.66 |
| 30 | 40.61 | 66.26 | 33.74 | 66.26 | 33.74 |
| 40 | 55.96 | 65.14 | 34.86 | 65.14 | 34.86 |
| 50 | 75.81 | 63.98 | 36.02 | 63.98 | 36.02 |
| 60 | 101.14 | 62.82 | 37.18 | 62.82 | 37.18 |
| 70 | 133.14 | 61.65 | 38.35 | 61.65 | 38.35 |
| 80 | 173.23 | 60.50 | 39.50 | 60.50 | 39.50 |
| 90 | 223.18 | 59.33 | 40.67 | 59.33 | 40.67 |
| 100 | 285.21 | 58.12 | 41.88 | 58.12 | 41.88 |
| 110 | 362.35 | 56.78 | 43.22 | 56.78 | 43.22 |
| 120 | 459.14 | 55.15 | 44.85 | 55.15 | 44.85 |
| 130 | 584.41 | 52.76 | 47.24 | 52.76 | 47.24 |
| 140 | 797.46 | 45.18 | 54.82 | 45.18 | 54.82 |

TABLE 8

| Azeotropic Temperature (° C.) | Azeotropic Pressure (psia) | Vapor-Phase Composition (Mass Percent) | | Liquid-Phase Composition (Mass Percent) | |
|---|---|---|---|---|---|
| | | HF | HFIB | HF | HFIB |
| −30 | 3.55 | 23.28 | 76.72 | 23.28 | 76.72 |
| −20 | 5.76 | 22.80 | 77.20 | 22.80 | 77.20 |
| −10 | 9.01 | 22.22 | 77.78 | 22.22 | 77.78 |
| 0 | 13.66 | 21.56 | 78.44 | 21.56 | 78.44 |
| 10 | 20.12 | 20.85 | 79.15 | 20.85 | 79.15 |
| 20 | 28.90 | 20.09 | 79.91 | 20.09 | 79.91 |
| 30 | 40.61 | 19.33 | 80.67 | 19.33 | 80.67 |
| 40 | 55.96 | 18.56 | 81.44 | 18.56 | 81.44 |
| 50 | 75.81 | 17.81 | 82.19 | 17.81 | 82.19 |
| 60 | 101.14 | 17.08 | 82.92 | 17.08 | 82.92 |

TABLE 8-continued

| Azeotropic Temperature (° C.) | Azeotropic Pressure (psia) | Vapor-Phase Composition (Mass Percent) | | Liquid-Phase Composition (Mass Percent) | |
|---|---|---|---|---|---|
| | | HF | HFIB | HF | HFIB |
| 70 | 133.14 | 16.39 | 83.61 | 16.39 | 83.61 |
| 80 | 173.23 | 15.74 | 84.26 | 15.74 | 84.26 |
| 90 | 223.18 | 15.10 | 84.90 | 15.10 | 84.90 |
| 100 | 285.21 | 14.47 | 85.53 | 14.47 | 85.53 |
| 110 | 362.35 | 13.81 | 86.19 | 13.81 | 86.19 |
| 120 | 459.14 | 13.04 | 86.96 | 13.04 | 86.96 |
| 130 | 584.41 | 11.99 | 88.01 | 11.99 | 88.01 |
| 140 | 797.46 | 9.13 | 90.87 | 9.13 | 90.87 |

Example 5. Azeotropic Compositions of Hydrogen Fluoride and 346Mdf

The calculated azeotropic and azeotrope-like ranges for HF/346mdf mixtures from −30° C. to 140° C. are summarized in Tables 9-10.

TABLE 9

| Azeotropic Temperature (° C.) | Azeotropic Pressure (psia) | Vapor-Phase Composition (Mole Percent) | | Liquid 1 Composition (Mole Percent) | | Liquid 2 Composition (Mole Percent) | |
|---|---|---|---|---|---|---|---|
| | | HF | 346mdf | HF | 346mdf | HF | 346mdf |
| −30 | 1.86 | 96.56 | 3.44 | 97.49 | 2.51 | 57.75 | 42.25 |
| −20 | 3.13 | 95.71 | 4.29 | 97.12 | 2.88 | 55.59 | 44.41 |
| −10 | 5.07 | 94.79 | 5.21 | 96.73 | 3.27 | 53.07 | 46.93 |
| 0 | 7.93 | 93.79 | 6.21 | 96.35 | 3.65 | 50.18 | 49.82 |
| 10 | 12.04 | 92.74 | 7.26 | 95.95 | 4.05 | 47.04 | 52.96 |
| 20 | 17.79 | 91.64 | 8.36 | 95.54 | 4.46 | 44.04 | 55.96 |
| 30 | 25.63 | 90.49 | 9.51 | 95.12 | 4.88 | 41.91 | 58.09 |
| 40 | 36.12 | 89.31 | 10.69 | 94.66 | 5.34 | 41.09 | 58.91 |
| 50 | 49.88 | 88.11 | 11.89 | 94.15 | 5.85 | 41.42 | 58.58 |
| 60 | 67.67 | 86.89 | 13.11 | 93.58 | 6.42 | 42.57 | 57.43 |
| 70 | 90.34 | 85.67 | 14.33 | 92.93 | 7.07 | 44.26 | 55.74 |
| 80 | 118.91 | 84.48 | 15.52 | 92.19 | 7.81 | 46.36 | 53.64 |
| 90 | 154.57 | 83.31 | 16.69 | 91.32 | 8.68 | 48.81 | 51.19 |
| 100 | 198.74 | 82.19 | 17.81 | 90.28 | 9.72 | 51.58 | 48.42 |
| 110 | 253.19 | 81.11 | 18.89 | 89.02 | 10.98 | 54.70 | 45.30 |
| 120 | 320.18 | 80.07 | 19.93 | 87.42 | 12.58 | 58.26 | 41.74 |
| 130 | 402.78 | 79.02 | 20.98 | 85.22 | 14.78 | 62.50 | 37.50 |
| 140 | 505.52 | 77.91 | 22.09 | 81.62 | 18.38 | 68.22 | 31.78 |

TABLE 10

| Azeotropic Temperature (° C.) | Azeotropic Pressure (psia) | Vapor-Phase Composition (Mass Percent) | | Liquid 1 Composition (Mass Percent) | | Liquid 2 Composition (Mass Percent) | |
|---|---|---|---|---|---|---|---|
| | | HF | 346mdf | HF | 346mdf | HF | 346mdf |
| −30 | 1.86 | 73.69 | 26.31 | 79.46 | 20.54 | 12.00 | 88.00 |
| −20 | 3.13 | 69.03 | 30.97 | 77.06 | 22.94 | 11.11 | 88.89 |
| −10 | 5.07 | 64.48 | 35.52 | 74.72 | 25.28 | 10.14 | 89.86 |
| 0 | 7.93 | 60.13 | 39.87 | 72.46 | 27.54 | 9.13 | 90.87 |
| 10 | 12.04 | 56.04 | 43.96 | 70.27 | 29.73 | 8.14 | 91.86 |
| 20 | 17.79 | 52.23 | 47.77 | 68.14 | 31.86 | 7.28 | 92.72 |
| 30 | 25.63 | 48.71 | 51.29 | 66.03 | 33.97 | 6.72 | 93.28 |
| 40 | 36.12 | 45.47 | 54.53 | 63.87 | 36.13 | 6.51 | 93.49 |
| 50 | 49.88 | 42.51 | 57.49 | 61.62 | 38.38 | 6.59 | 93.41 |
| 60 | 67.67 | 39.81 | 60.19 | 59.25 | 40.75 | 6.89 | 93.11 |
| 70 | 90.34 | 37.37 | 62.63 | 56.74 | 43.26 | 7.34 | 92.66 |
| 80 | 118.91 | 35.19 | 64.81 | 54.07 | 45.93 | 7.94 | 92.06 |
| 90 | 154.57 | 33.25 | 66.75 | 51.20 | 48.80 | 8.69 | 91.31 |
| 100 | 198.74 | 31.53 | 68.47 | 48.10 | 51.90 | 9.61 | 90.39 |
| 110 | 253.19 | 30.00 | 70.00 | 44.72 | 55.28 | 10.75 | 89.25 |
| 120 | 320.18 | 28.61 | 71.39 | 40.94 | 59.06 | 12.23 | 87.77 |
| 130 | 402.78 | 27.32 | 72.68 | 36.53 | 63.47 | 14.26 | 85.74 |
| 140 | 505.52 | 26.04 | 73.96 | 30.70 | 69.30 | 17.64 | 82.36 |

Example 6. Azeotropic Compositions of Hydrogen Fluoride and 347Mef

The calculated azeotropic and azeotrope-like ranges for HF/347mef mixtures from −30° C. to 140° C. are summarized in Tables 11-12.

TABLE 11

| Azeotropic Temperature (° C.) | Azeotropic Pressure (psia) | Vapor-Phase Composition (Mole Percent) | | Liquid 1 Composition (Mole Percent) | | Liquid 2 Composition (Mole Percent) | |
|---|---|---|---|---|---|---|---|
| | | HF | 347mef | HF | 347mef | HF | 347mef |
| −30 | 2.50 | 88.05 | 11.95 | 97.49 | 2.51 | 57.75 | 42.25 |
| −20 | 4.25 | 86.59 | 13.41 | 97.12 | 2.88 | 55.59 | 44.41 |
| −10 | 6.94 | 85.13 | 14.87 | 96.73 | 3.27 | 53.07 | 46.93 |
| 0 | 10.89 | 83.69 | 16.31 | 96.35 | 3.65 | 50.18 | 49.82 |
| 10 | 16.52 | 82.29 | 17.71 | 95.95 | 4.05 | 47.04 | 52.96 |
| 20 | 24.31 | 80.92 | 19.08 | 95.54 | 4.46 | 44.04 | 55.96 |
| 30 | 34.82 | 79.59 | 20.41 | 95.12 | 4.88 | 41.91 | 58.09 |
| 40 | 48.71 | 78.29 | 21.71 | 94.66 | 5.34 | 41.09 | 58.91 |
| 50 | 66.73 | 77.03 | 22.97 | 94.15 | 5.85 | 41.42 | 58.58 |
| 60 | 89.76 | 75.81 | 24.19 | 93.58 | 6.42 | 42.57 | 57.43 |
| 70 | 118.82 | 74.66 | 25.34 | 92.93 | 7.07 | 44.26 | 55.74 |
| 80 | 155.12 | 73.58 | 26.42 | 92.19 | 7.81 | 46.36 | 53.64 |
| 90 | 200.13 | 72.58 | 27.42 | 91.32 | 8.68 | 48.81 | 51.19 |
| 100 | 255.69 | 71.66 | 28.34 | 90.28 | 9.72 | 51.58 | 48.42 |
| 110 | 324.30 | 70.81 | 29.19 | 89.02 | 10.98 | 54.70 | 45.30 |
| 120 | 409.53 | 70.00 | 30.00 | 87.42 | 12.58 | 58.26 | 41.74 |
| 130 | 517.43 | 69.14 | 30.86 | 85.22 | 14.78 | 62.50 | 37.50 |
| 140 | 660.67 | 68.16 | 31.84 | 68.16 | 31.84 | — | — |

TABLE 12

| Azeotropic Temperature (° C.) | Azeotropic Pressure (psia) | Vapor-Phase Composition (Mass Percent) | | Liquid 1 Composition (Mass Percent) | | Liquid 2 Composition (Mass Percent) | |
|---|---|---|---|---|---|---|---|
| | | HF | 347mef | HF | 347mef | HF | 347mef |
| −30 | 2.50 | 44.47 | 55.53 | 80.82 | 19.18 | 12.94 | 87.06 |
| −20 | 4.25 | 41.24 | 58.76 | 78.54 | 21.46 | 11.98 | 88.02 |
| −10 | 6.94 | 38.36 | 61.64 | 76.30 | 23.70 | 10.95 | 89.05 |
| 0 | 10.89 | 35.81 | 64.19 | 74.13 | 25.87 | 9.87 | 90.13 |
| 10 | 16.52 | 33.56 | 66.44 | 72.03 | 27.97 | 8.80 | 91.20 |
| 20 | 24.31 | 31.56 | 68.44 | 69.97 | 30.03 | 7.88 | 92.12 |
| 30 | 34.82 | 29.77 | 70.23 | 67.92 | 32.08 | 7.27 | 92.73 |
| 40 | 48.71 | 28.16 | 71.84 | 65.82 | 34.18 | 7.05 | 92.95 |
| 50 | 66.73 | 26.71 | 73.29 | 63.62 | 36.38 | 7.14 | 92.86 |
| 60 | 89.76 | 25.41 | 74.59 | 61.30 | 38.70 | 7.46 | 92.54 |
| 70 | 118.82 | 24.26 | 75.74 | 58.83 | 41.17 | 7.95 | 92.05 |
| 80 | 155.12 | 23.24 | 76.76 | 56.19 | 43.81 | 8.59 | 91.41 |
| 90 | 200.13 | 22.35 | 77.65 | 53.34 | 46.66 | 9.39 | 90.61 |
| 100 | 255.69 | 21.56 | 78.44 | 50.24 | 49.76 | 10.38 | 89.62 |
| 110 | 324.30 | 20.87 | 79.13 | 46.84 | 53.16 | 11.60 | 88.40 |
| 120 | 409.53 | 20.23 | 79.77 | 43.02 | 56.98 | 13.18 | 86.82 |
| 130 | 517.43 | 19.58 | 80.42 | 38.54 | 61.46 | 15.34 | 84.66 |
| 140 | 660.67 | 18.87 | 81.13 | 18.87 | 81.13 | — | — |

Example 7. Azeotropic Compositions of Hydrogen Fluoride and 356Mff

The calculated azeotropic ranges for HF/356mff mixtures from −30° C. to 140° C. are summarized in Tables 13-14.

TABLE 13

| Azeotropic Temperature | Azeotropic Pressure | Vapor-Phase Composition (Mole Percent) | | Liquid-Phase Composition (Mole Percent) | |
|---|---|---|---|---|---|
| (° C.) | (psia) | HF | 356mff | HF | 356mff |
| −30 | 2.41 | 83.67 | 16.33 | 83.67 | 16.33 |
| −20 | 4.10 | 81.87 | 18.13 | 81.87 | 18.13 |
| −10 | 6.67 | 80.03 | 19.97 | 80.03 | 19.97 |
| 0 | 10.46 | 78.15 | 21.85 | 78.15 | 21.85 |
| 10 | 15.88 | 76.27 | 23.73 | 76.27 | 23.73 |
| 20 | 23.41 | 74.40 | 25.60 | 74.40 | 25.60 |
| 30 | 33.61 | 72.56 | 27.44 | 72.56 | 27.44 |
| 40 | 47.13 | 70.78 | 29.22 | 70.78 | 29.22 |
| 50 | 64.72 | 69.08 | 30.92 | 69.08 | 30.92 |
| 60 | 87.20 | 67.47 | 32.53 | 67.47 | 32.53 |
| 70 | 115.52 | 65.98 | 34.02 | 65.98 | 34.02 |
| 80 | 150.76 | 64.60 | 35.40 | 64.60 | 35.40 |
| 90 | 194.14 | 63.34 | 36.66 | 63.34 | 36.66 |
| 100 | 247.05 | 62.17 | 37.83 | 62.17 | 37.83 |
| 110 | 311.13 | 61.08 | 38.92 | 61.08 | 38.92 |
| 120 | 388.31 | 60.00 | 40.00 | 60.00 | 40.00 |
| 130 | 480.97 | 58.86 | 41.14 | 58.86 | 41.14 |
| 140 | 592.66 | 57.47 | 42.53 | 57.47 | 42.53 |

TABLE 14

| Azeotropic Temperature | Azeotropic Pressure | Vapor-Phase Composition (Mass Percent) | | Liquid-Phase Composition (Mass Percent) | |
|---|---|---|---|---|---|
| (° C.) | (psia) | HF | 356mff | HF | 356mff |
| −30 | 2.41 | 38.17 | 61.83 | 38.17 | 61.83 |
| −20 | 4.10 | 35.24 | 64.76 | 35.24 | 64.76 |
| −10 | 6.67 | 32.56 | 67.44 | 32.56 | 67.44 |
| 0 | 10.46 | 30.12 | 69.88 | 30.12 | 69.88 |
| 10 | 15.88 | 27.91 | 72.09 | 27.91 | 72.09 |
| 20 | 23.41 | 25.93 | 74.07 | 25.93 | 74.07 |
| 30 | 33.61 | 24.16 | 75.84 | 24.16 | 75.84 |
| 40 | 47.13 | 22.59 | 77.41 | 22.59 | 77.41 |
| 50 | 64.72 | 21.21 | 78.79 | 21.21 | 78.79 |
| 60 | 87.20 | 20.00 | 80.00 | 20.00 | 80.00 |
| 70 | 115.52 | 18.94 | 81.06 | 18.94 | 81.06 |
| 80 | 150.76 | 18.02 | 81.98 | 18.02 | 81.98 |
| 90 | 194.14 | 17.23 | 82.77 | 17.23 | 82.77 |
| 100 | 247.05 | 16.53 | 83.47 | 16.53 | 83.47 |
| 110 | 311.13 | 15.90 | 84.10 | 15.90 | 84.10 |

TABLE 14-continued

| Azeotropic Temperature | Azeotropic Pressure | Vapor-Phase Composition (Mass Percent) | | Liquid-Phase Composition (Mass Percent) | |
|---|---|---|---|---|---|
| (° C.) | (psia) | HF | 356mff | HF | 356mff |
| 120 | 388.31 | 15.31 | 84.69 | 15.31 | 84.69 |
| 130 | 480.97 | 14.70 | 85.30 | 14.70 | 85.30 |
| 140 | 592.66 | 14.00 | 86.00 | 14.00 | 86.00 |

Example 8. Separation of HCFC-346Mdf from HF Utilizing Azeotropic Distillation

Figure 2:
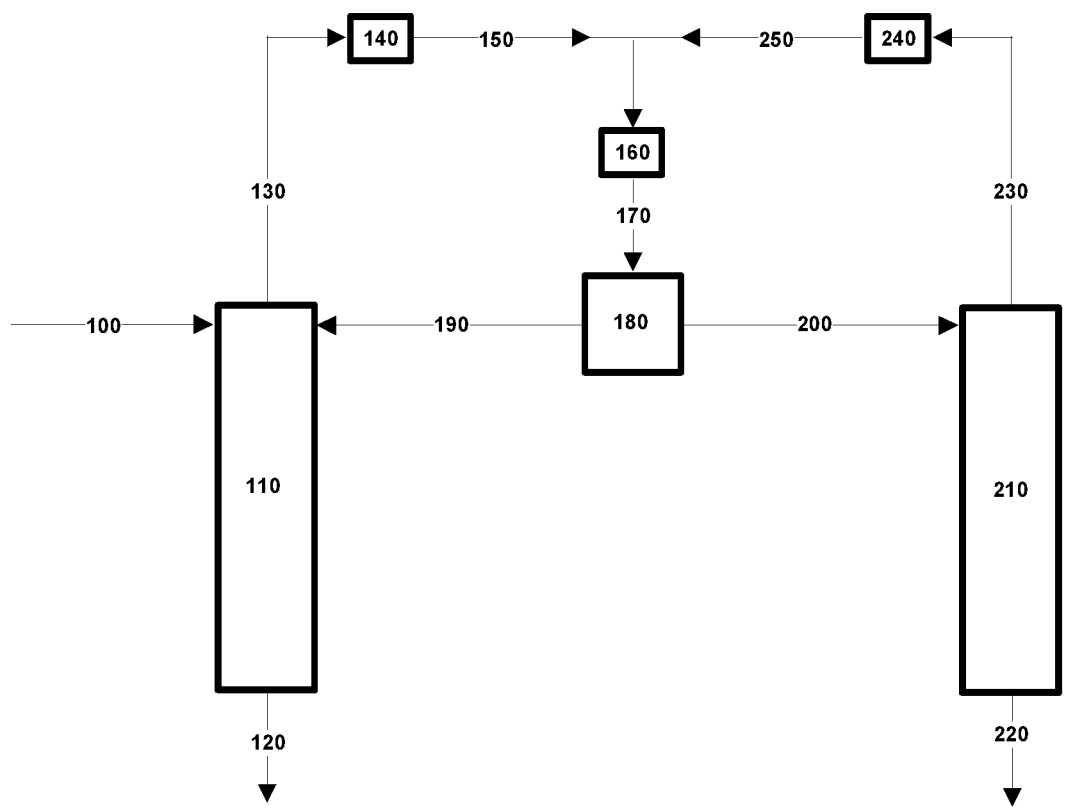
FIG. 2 shows an exemplary system useful for separating heterogeneous azeotropes formed by compounds of Formula I from hydrogen fluoride via azeotropic distillation.

As described above in Example 5, HCFC-346mdf and HF form a minimum-boiling azeotrope. The following data demonstrates that because the HF/HCFC-346mdf azeotrope is heterogeneous, HF may be separated from HCFC-346mdf by azeotropic distillation. Referring to FIG. 2, a composition comprising HF and HCFC-346mdf is fed to a first column 110 via stream 100. The first column 110 contains 10 theoretical stages and is operated under appropriate conditions to approach the low-boiling HF/HCFC-346mdf azeotrope. Because HCFC-346mdf is being fed to first column 110 in excess of the concentration needed to form the azeotrope with the HF, HCFC-346mdf, essentially free of HF, is recovered as a product stream from the bottom of the column via stream 120, while a composition near to the HF/HCFC-346mdf azeotrope is recovered as distillate via stream 130. Stream 130 is condensed in condenser 140, mixed with the near azeotropic composition recycled from the second column via stream 250 and the combined stream is sub-cooled in cooler 160 and sent to decanter 180 where the combined stream 170 separates into separate HCFC-346mdf-rich 190 and HF-rich 200 streams. Stream 190 is recycled to the first column as reflux. Stream 200 is fed to the top stage of a second distillation column 210, containing 20 theoretical stages and operated under conditions to approach the HF/HCFC-346mdf azeotrope. Because HF is being fed to this second column in excess of the concentration needed to form the low-boiling HF/HCFC-346mdf azeotrope, HF, essentially free of HCFC-346mdf, is recovered as a product stream from the bottom of the column via stream 220 while a composition close to the HF/HCFC-346mdf azeotrope is recovered as distillate via stream 230. Stream 230 is condensed in condenser 240, mixed with the near azeotropic composition from the first column via stream 150 and fed to cooler 160 and then decanter 180.

The data in Table 15 were calculated using measured and calculated thermodynamic properties.

TABLE 15

| | First column feed | First column distillate | First column bottoms (346mdf product) | 346mdf rich decanter phase | HF-rich decanter phase | Second column distillate | Second column bottoms |
|---|---|---|---|---|---|---|---|
| Stream No. (FIG. 2) | 100 | 130 | 120 | 190 | 200 | 230 | 220 |
| HF (wt %) | 50 | 40.2 | <1 ppm | 6.5 | 62.8 | 40.6 | 100 |
| 346mdf (wt %) | 50 | 59.8 | 100 | 93.5 | 37.2 | 59.4 | <1 ppm |
| Temperature (° C.) | 35.0 | 58.5 | 101.8 | 45.0 | 45.0 | 58.6 | 66.7 |
| Pressure (Psia) | 74.7 | 64.7 | 64.8 | 64.6 | 64.6 | 64.7 | 64.8 |

The other heterogeneous azeotropes described in the Examples provided herein above can be separated by analogous procedures.

Example 9. Separation of HFO-E-1336Mzz and HFO-Z-1336Mzz from HF Utilizing Azeotropic Distillation This example describes how a first minimum-boiling HF azeotrope can be used to remove HF from a second, higher-boiling, HF azeotrope, thereby recovering the second non-HF compound in the second HF azeotrope essentially free of HF. The first and second HF azeotropes can each be homogeneous or heterogeneous, though preferably, the first, lower-boiling azeotrope is heterogeneous. The process configuration shown in FIG. 3 presumes the first HF azeotrope is heterogeneous. The compound forming the first HF azeotrope can either be present in the mixture to be separated or added to the first distillation column of the separation system.

Figure 3:
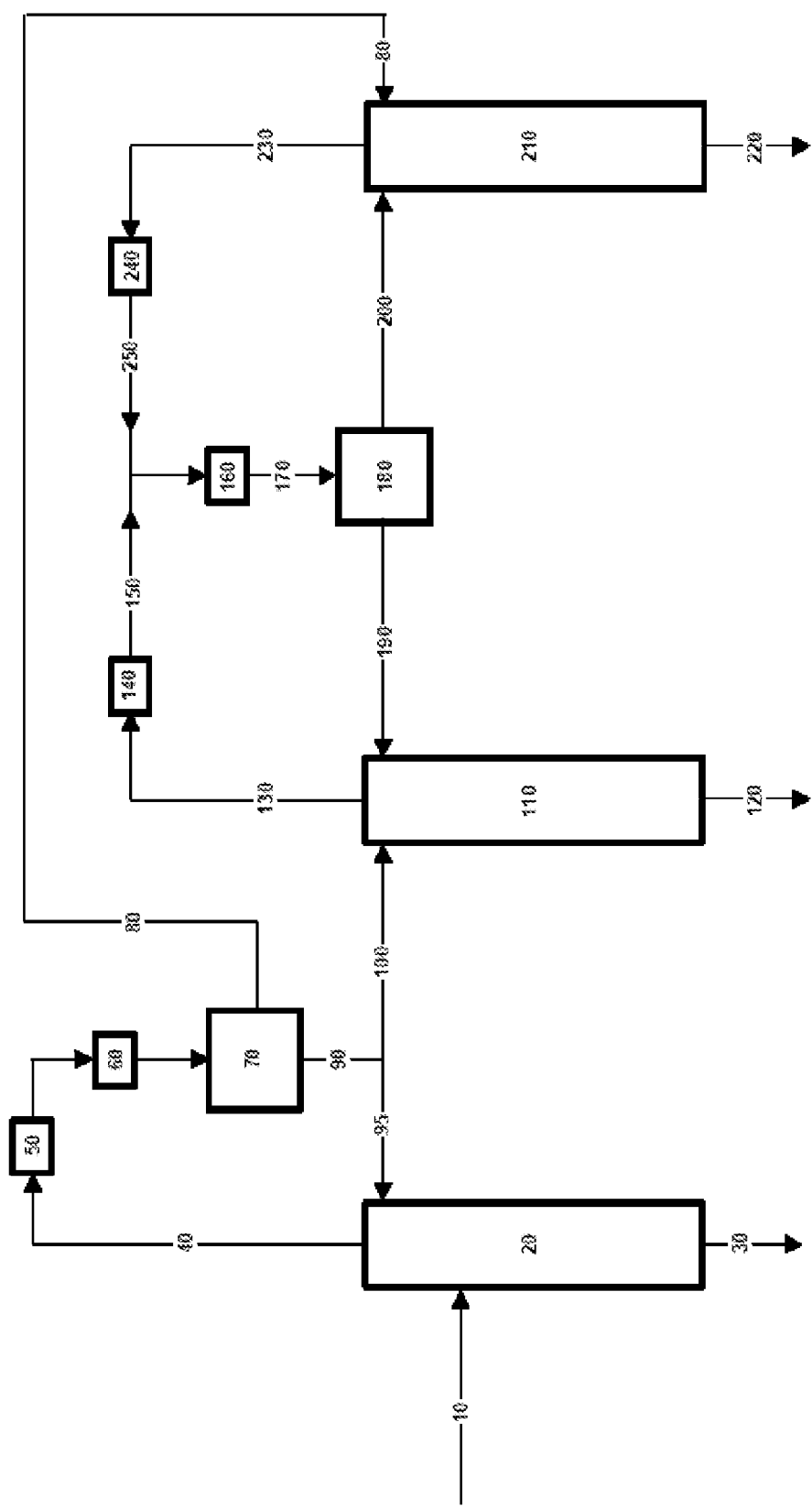
FIG. 3 shows a second exemplary system useful for separating compounds of Formula I from hydrogen fluoride utilizing a first minimum-boiling heterogeneous HF azeotrope to remove HF from a second, higher-boiling HF azeotrope, followed by separation of the first HF azeotrope by a method similar to the azeotropic distillation of FIG. 2.

Referring to FIG. 3, a stream comprising HF, HFO-E-1336mzz (E-1336mzz), and HFO-Z-1336mzz (Z-1336mzz) is fed via stream 10 to the $32^{nd}$ theoretical stage from the top of a first distillation column 20 containing 40 theoretical stages. The lower boiling azeotrope formed by E-1336mzz and HF is used to separate the Z-1336mzz present in this first distillation column 20. Should the feed mixture not contain enough E-1336mzz to cause all of the HF to distill overhead, supplemental E-1336mzz in an amount sufficient to cause all of the HF to distill away from the Z-1336mzz is added by increasing the flowrate of E-1336mzz-enriched stream 95 which is added to the top of the first column 20 as reflux. Column 20 is operated under conditions to approach the lower-boiling HF/E-1336mzz azeotrope at the top of the column, which is removed as distillate via stream 40. An essentially HF-free mixture comprising Z-1336mzz is removed from the bottom of column 20 via stream 30. Distillate stream 40 is condensed in a first condenser 50, optionally further cooled in a first cooler 60, and then sent to a first decanter 70 operated such that the now liquid distillate separates into HF-rich and E-1336mzz-rich liquid phase fractions in the decanter, which are removed via streams 80 and 90, respectively. A portion of the E-1336mzz-rich stream 90 is returned to the top of the first column via stream 95 as reflux and as the source of supplemental E-1336mzz previously described. The remaining portion is fed to a second distillation column 110 via stream 100 where it is separated into an E-1336mzz bottom product stream 120, that is essentially free of HF, and a distillate 130 with a composition near the HF/E-1336mzz azeotrope. Because reflux stream 95 is enriched in E-1336mzz relative to the E-1336mzz/HF azeotropic composition, this stream can supply the additional E-1336mzz needed to make the Z-1336mzz bottoms product 30 from the first column essentially free of HF. For the feed composition used in this example, a reflux to feed mass flowrate ratio of 4.0 ensures that stream 30 is essentially free of HF.

The HF-rich phase fraction from the first decanter is fed to a third distillation column 210 via stream 80. Both feeds (80 and 200) to the third column have compositions containing excess HF relative to the HF/E-1336mzz azeotrope enabling an HF bottoms product 220, essentially free of E-1336mzz and Z-1336mzz, to be produced in column 210. The third column distillate has a composition near the HF/E-1336mzz azeotrope and is removed via stream 230. The second and third distillate streams 130 and 230 from columns 110 and 210 are condensed in condensers 140 and 240, forming streams 150 and 250, respectively, mixed together, and sent first to an optional second cooler 160 and then to a second decanter 180 where separate E-1336mzz-rich and HF-rich liquid phase fractions are formed. The E-1336mzz-rich fraction removed from decanter 180 via stream 190 is returned to the top of the second column 110 as reflux and for further separation. The HF-rich fraction removed from decanter 180 via stream 200 is fed to the top of the third column 210 as reflux and for further separation.

The data in Table 16 were obtained by calculation using measured and calculated thermodynamic properties.

TABLE 16

| | Feed | $1^{st}$ Btm. | $1^{st}$ Dist. | $1^{st}$ HF-rich phase | $1^{st}$ E-1336mzz - rich phase | $2^{nd}$ Btm. | $2^{nd}$ Dist. | $3^{rd}$ Btm. | $3^{rd}$ Dist. |
|---|---|---|---|---|---|---|---|---|---|
| Stream # (FIG. 3) | 10 | 30 | 40 | 80 | 90 | 120 | 130 | 220 | 230 |
| HF (wt %) | 7.5 | <1 ppm | 8.7 | 42.7 | 7.7 | <1 ppm | 15.5 | 100 | 15.8 |
| E-1336mzz (wt %) | 30.8 | 70 ppm | 91.3 | 57.3 | 92.3 | 100 | 84.5 | <1 ppm | 84.2 |
| Z-1336mzz (wt %) | 61.7 | 100 | 1 ppm | <1 ppm | 1 ppm | 1 ppm | <1 ppm | <1 ppm | <1 ppm |
| Temperature (° C.) | 37.0 | 90.0 | 46.6 | 40.0 | 40.0 | 56.2 | 41.8 | 72.0 | 42.0 |
| Pressure (psia) | 84.7 | 80.4 | 79.7 | 79.7 | 79.7 | 74.8 | 74.7 | 74.8 | 74.7 |

OTHER EMBODIMENTS

1. In some embodiments, the present application provides a composition, comprising:
    i) hydrogen fluoride; and
    ii) a compound of Formula I:

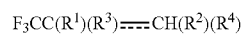

$$F_3CC(R^1)(R^3)\text{\textequals\textequals\textequals}CH(R^2)(R^4) \qquad I$$

wherein ═══ refers to a single bond or a double bond;
$R^1$ is H, halo, or $C_{1-3}$ haloalkyl;
$R^2$ is H or $C_{1-3}$ haloalkyl; and ═══
$R^3$ and $R^4$ are each H; or alternatively, $R^3$ and $R^4$ are absent when ═══ forms a double bond;
wherein the compound of Formula I is present in an amount effective to form an azeotrope composition or an azeotrope-like composition with the hydrogen fluoride.

2. The composition of embodiment 1, wherein $R^1$ is H, halo, or $C_{1-3}$ fluoroalkyl.

3. The composition of embodiment 1, wherein $R^1$ is H, chloro, fluoro, or trifluoromethyl.

4. The composition of any one of embodiments 1 to 3, wherein $R^2$ is H or $C_{1-3}$ fluoroalkyl.

5. The composition of any one of embodiments 1 to 3, wherein $R^2$ is H or trifluoromethyl.

6. The composition of any one of embodiments 1 to 5, wherein the compound of Formula I is a compound of Formula Ia:

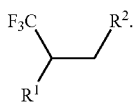

7. The composition of any one of embodiments 1 to 5, wherein the compound of Formula I is a compound of Formula Ib or Formula Ic:

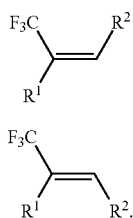

8. The composition of any one of embodiments 1, 6, and 7, wherein the compound of Formula I is selected from the group consisting of:
1,1,1,4,4,4-hexafluorobut-2-ene;
3,3,3-trifluoro-2-(trifluoromethyl)prop-1-ene;
2-chloro-1,1,1,4,4,4-hexafluorobutane;
1,1,1,2,4,4,4-heptafluorobutane; and
1,1,1,4,4,4-hexafluorobutane;
wherein the compound of Formula I is present in an amount effective to form an azeotrope or an azeotrope-like composition with the hydrogen fluoride.

9. The composition of any one of embodiments 1, 6, and 7, wherein the compound of Formula I is selected from the group consisting of:
(E)-1,1,1,4,4,4-hexafluorobut-2-ene;
(Z)-1,1,1,4,4,4-hexafluorobut-2-ene;
3,3,3-trifluoro-2-(trifluoromethyl)prop-1-ene;
2-chloro-1,1,1,4,4,4-hexafluorobutane;
1,1,1,2,4,4,4-heptafluorobutane; and
1,1,1,4,4,4-hexafluorobutane;
wherein the compound of Formula I is present in an amount effective to form an azeotrope or an azeotrope-like composition with the hydrogen fluoride.

10. The composition of embodiment 1 or 7, wherein the compound of Formula I is (E)-1,1,1,4,4,4-hexafluorobut-2-ene, wherein the (E)-1,1,1,4,4,4-hexafluorobut-2-ene is present in an amount effective to form an azeotrope or an azeotrope-like composition with the hydrogen fluoride.

11. The composition of embodiment 10, wherein the composition comprises from about 52 to about 76 mole percent hydrogen fluoride and from about 48 to about 24 mole percent (E)-1,1,1,4,4,4-hexafluorobut-2-ene.

12. The composition of embodiment 10 or 11, wherein the composition has a boiling point of from about −30° C. to about 110° C. at a pressure of from about 3 psia to about 812 psia.

13. The composition of embodiment 1 or 7, wherein the compound of Formula I is (Z)-1,1,1,4,4,4-hexafluorobut-2-ene, wherein the (Z)-1,1,1,4,4,4-hexafluorobut-2-ene is present in an amount effective to form an azeotrope or an azeotrope-like composition with the hydrogen fluoride.

14. The composition of embodiment 13, wherein the composition comprises from about 59 to about 92 mole percent hydrogen fluoride and from about 41 to about 8 mole percent (Z)-1,1,1,4,4,4-hexafluorobut-2-ene.

15. The composition of embodiment 13 or 14, wherein the composition has a boiling point of from about −30° C. to about 130° C. at a pressure of from about 2 psia to about 836 psia.

16. The composition of embodiment 1 or 7, wherein the compound of Formula I is 3,3,3-trifluoro-2-(trifluoromethyl)prop-1-ene, wherein the 3,3,3-trifluoro-2-(trifluoromethyl)prop-1-ene is present in an amount effective to form an azeotrope or an azeotrope-like composition with the hydrogen fluoride.

17. The composition of embodiment 16, wherein the composition comprises from about 45 to about 72 mole percent hydrogen fluoride and from about 55 to about 28 mole percent 3,3,3-trifluoro-2-(trifluoromethyl)prop-1-ene.

18. The composition of embodiment 16 or 17, wherein the composition has a boiling point of from about −30° C. to about 140° C. at a pressure of from about 3 psia to about 800 psia.

19. The composition of embodiment 1 or 6, wherein the compound of Formula I is 2-chloro-1,1,1,4,4,4-hexafluorobutane, wherein the 2-chloro-1,1,1,4,4,4-hexafluorobutane is present in an amount effective to form an azeotrope or an azeotrope-like composition with the hydrogen fluoride.

20. The composition of embodiment 19, wherein the composition comprises from about 77 to about 97 mole percent hydrogen fluoride and from about 23 to about 3 mole percent 2-chloro-1,1,1,4,4,4-hexafluorobutane.

21. The composition of embodiment 19 or 20, wherein the composition has a boiling point of from about −30° C. to about 140° C. at a pressure of from about 1 psia to about 510 psia.

22. The composition of embodiment 1 or 6, wherein the compound of Formula I is 1,1,1,2,4,4,4-heptafluorobutane, wherein the 1,1,1,2,4,4,4-heptafluorobutane is present in an amount effective to form an azeotrope or an azeotrope-like composition with the hydrogen fluoride.

23. The composition of embodiment 22, wherein the composition comprises from about 68 to about 89 mole percent hydrogen fluoride and from about 32 to about 11 mole percent 1,1,1,2,4,4,4-heptafluorobutane.

24. The composition of embodiment 22 or 23, wherein the composition has a boiling point of from about −30° C. to about 140° C. at a pressure of from about 1 psia to about 665 psia.

25. The composition of embodiment 1 or 6, wherein the compound of Formula I is 1,1,1,4,4,4-hexafluorobutane, wherein the 1,1,1,4,4,4-hexafluorobutane is present in an amount effective to form an azeotrope or an azeotrope-like composition with the hydrogen fluoride.

26. The composition of embodiment 25, wherein the composition comprises from about 57 to about 84 mole percent hydrogen fluoride and from about 43 to about 16 mole percent 1,1,1,4,4,4-hexafluorobutane.

27. The composition of embodiment 25 or 26, wherein the composition has a boiling point of from about −30° C. to about 140° C. at a pressure of from about 1 psia to about 600 psia.

28. The composition of any one of embodiments 1, 6, or 7, wherein the composition comprises:
from about 52 to about 76 mole percent hydrogen fluoride and from about 48 to about 24 mole percent (E)-1,1,1,4,4-hexafluorobut-2-ene, wherein the composition has a boiling point of from about −30° C. to about 110° C. at a pressure of from about 3 psia to about 812 psia; or from about 59 to about 92 mole percent hydrogen fluoride and from about 41 to about 8 mole percent (Z)-1,1,1,4,4,4-hexafluorobut-2-ene, wherein the composition has a boiling point of from about −30° C. to about 130° C. at a pressure of from about 2 psia to about 836 psia; or from about 45 to about 72 mole percent hydrogen fluoride and from about 55 to about 28 mole percent 3,3,3-trifluoro-2-(trifluoromethyl)prop-1-ene, wherein the composition has a boiling point of from about −30° C. to about 140° C. at a pressure of from about 3 psia to about 800 psia; or from about 77 to about 97 mole percent hydrogen fluoride and from about 23 to about 3 mole percent 2-chloro-1,1,1,4,4,4-hexafluorobutane, wherein the composition has a boiling point of from about −30° C. to about 140° C. at a pressure of from about 1 psia to about 510 psia; or from about 68 to about 89 mole percent hydrogen fluoride and from about 32 to about 11 mole percent 1,1,1,2,4,4,4-heptafluorobutane, wherein the composition has a boiling point of from about −30° C. to about 140° C. at a pressure of from about 1 psia to about 665 psia; or from about 57 to about 84 mole percent hydrogen fluoride and from about 43 to about 16 mole percent 1,1,1,4,4,4-hexafluorobutane, wherein the composition has a boiling point of from about −30° C. to about 140° C. at a pressure of from about 1 psia to about 600 psia.

29. The composition of any one of embodiments 1 to 18 and 25 to 28, wherein the composition is a homogeneous azeotrope or azeotrope-like composition.

30. The composition of any one of embodiments 1 to 15, 19 to 24, and 28, wherein the composition is a heterogeneous azeotrope or azeotrope-like composition.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims. It should be appreciated by those persons having ordinary skill in the art(s) to which the present invention relates that any of the features described herein in respect of any particular aspect and/or embodiment of the present invention can be combined with one or more of any of the other features of any other aspects and/or embodiments of the present invention described herein, with modifications as appropriate to ensure compatibility of the combinations. Such combinations are considered to be part of the present invention contemplated by this disclosure.

What is claimed is:

1. A composition comprising hydrogen fluoride and a compound selected from the group consisting of:
3,3,3-trifluoro-2-(trifluoromethyl)prop-1-ene;
2-chloro-1,1,1,4,4,4-hexafluorobutane; and
1,1,1,2,4,4,4-heptafluorobutane;
wherein the 3,3,3-trifluoro-2-(trifluoromethyl)prop-1-ene, 2-chloro-1,1,1,4,4,4-hexafluorobutane, or 1,1,1,2,4,4,4-heptafluorobutane is present in an amount effective to form an azeotrope or an azeotrope-like composition with the hydrogen fluoride.

2. The composition of claim 1, wherein the composition comprises hydrogen fluoride and 3,3,3-trifluoro-2-(trifluoromethyl)prop-1-ene, wherein the 3,3,3-trifluoro-2-(trifluoromethyl)prop-1-ene is present in an amount effective to form an azeotrope or an azeotrope-like composition with the hydrogen fluoride.

3. The composition of claim 2, wherein the composition comprises from about 45 to about 72 mole percent hydrogen fluoride and from about 55 to about 28 mole percent 3,3,3-trifluoro-2-(trifluoromethyl)prop-1-ene.

4. The composition of claim 3, wherein the composition has a boiling point of from about −30° C. to about 140° C. at a pressure of from about 3 psia to about 800 psia.

5. The composition of claim 2, wherein the is a homogeneous azeotrope composition or a homogeneous azeotrope-like composition.

6. The composition of claim 1, wherein the composition comprises hydrogen fluoride and 2-chloro-1,1,1,4,4,4-hexafluorobutane, wherein the 2-chloro-1,1,1,4,4,4-hexafluorobutane is present in an amount effective to form an azeotrope or an azeotrope-like composition with the hydrogen fluoride.

7. The composition of claim 6, wherein the composition comprises from about 77 to about 97 mole percent hydrogen fluoride and from about 23 to about 3 mole percent 2-chloro-1,1,1,4,4,4-hexafluorobutane.

8. The composition of claim 7, wherein the composition has a boiling point of from about −30° C. to about 140° C. at a pressure of from about 1 psia to about 510 psia.

9. The composition of claim 6, wherein the composition is a heterogeneous azeotrope composition or a heterogeneous azeotrope-like composition.

10. The composition of claim 1, wherein the composition comprises hydrogen fluoride and 1,1,1,2,4,4,4-heptafluorobutane, wherein the 1,1,1,2,4,4,4-heptafluorobutane is present in an amount effective to form an azeotrope or an azeotrope-like composition with the hydrogen fluoride.

11. The composition of claim 10, wherein the composition comprises from about 68 to about 89 mole percent hydrogen fluoride and from about 32 to about 11 mole percent 1,1,1,2,4,4,4-heptafluorobutane.

12. The composition of claim 11, wherein the composition has a boiling point of from about −30° C. to about 140° C. at a pressure of from about 1 psia to about 665 psia.

13. The composition of claim 10, wherein the composition is a heterogeneous azeotrope composition or a heterogeneous azeotrope-like composition.

14. The composition of claim 1, wherein the composition is a homogeneous azeotrope composition or a homogeneous azeotrope-like composition.

15. The composition of claim 1, wherein the composition is a heterogeneous azeotrope composition or a heterogeneous azeotrope-like composition.

16. A composition, comprising from about 52 to about 76 mole percent hydrogen fluoride and from about 48 to about 24 mole percent (E)-1,1,1,4,4,4-hexafluorobut-2-ene, wherein the (E)-1,1,1,4,4,4-hexafluorobut-2-ene is present in an amount effective to form an azeotrope or an azeotrope-like composition with the hydrogen fluoride.

17. The composition of claim 16, wherein the composition has a boiling point of from about −30° C. to about 110° C. at a pressure of from about 3 psia to about 812 psia.

18. The composition of claim 16, wherein the composition is a homogeneous azeotrope composition or a homogeneous azeotrope-like composition.

19. The composition of claim 16, wherein the composition is a heterogeneous azeotrope composition or a heterogeneous azeotrope-like composition.

20. A composition, comprising from about 59 to about 92 mole percent hydrogen fluoride and from about 41 to about 8 mole percent (Z)-1,1,1,4,4,4-hexafluorobut-2-ene, wherein the (Z)-1,1,1,4,4,4-hexafluorobut-2-ene is present in an amount effective to form an azeotrope or an azeotrope-like composition with the hydrogen fluoride.

21. The composition of claim 20, wherein the composition has a boiling point of from about −30° C. to about 130° C. at a pressure of from about 2 psia to about 836 psia.

22. The composition of claim 20, wherein the is a homogeneous azeotrope composition or a homogeneous azeotrope-like composition.

23. The composition of claim 20, wherein the composition is a heterogeneous azeotrope composition or a heterogeneous azeotrope-like composition.

* * * * *